United States Patent
Qin et al.

(10) Patent No.: US 9,951,112 B2
(45) Date of Patent: Apr. 24, 2018

(54) BMP-4 PEPTIDES AND METHODS OF USE

(75) Inventors: Xiaofei Qin, Virginia Beach, VA (US); Silvia Chen, Virginia Beach, VA (US); Jingsong Chen, Virginia Beach, VA (US); James Clagett, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

(21) Appl. No.: 13/636,870

(22) PCT Filed: Mar. 24, 2011

(86) PCT No.: PCT/US2011/029789
§ 371 (c)(1),
(2), (4) Date: Dec. 10, 2012

(87) PCT Pub. No.: WO2011/119829
PCT Pub. Date: Sep. 29, 2011

(65) Prior Publication Data
US 2013/0196910 A1    Aug. 1, 2013

Related U.S. Application Data

(60) Provisional application No. 61/317,075, filed on Mar. 24, 2010.

(51) Int. Cl.
| | |
|---|---|
| *A61K 38/17* | (2006.01) |
| *A61K 38/18* | (2006.01) |
| *A61K 38/48* | (2006.01) |
| *C07K 14/51* | (2006.01) |
| *C07K 1/00* | (2006.01) |
| *C12N 9/48* | (2006.01) |
| *C12N 5/077* | (2010.01) |
| *C12N 5/071* | (2010.01) |
| *A61K 38/00* | (2006.01) |

(52) U.S. Cl.
CPC .......... *C07K 14/51* (2013.01); *A61K 38/1875* (2013.01); *A61K 38/48* (2013.01); *C12N 5/0602* (2013.01); *C12N 5/0658* (2013.01); *C12N 9/48* (2013.01); *A61K 38/00* (2013.01); *C12N 2501/155* (2013.01)

(58) Field of Classification Search
None
See application file for complete search history.

(56) References Cited

U.S. PATENT DOCUMENTS

| | | | |
|---|---|---|---|
| 6,352,972 B1* | 3/2002 | Nimni et al. | 514/8.8 |
| 2005/0187162 A1 | 8/2005 | Dhanaraj et al. | |
| 2006/0280768 A1* | 12/2006 | Hwang | A61B 17/064 424/423 |
| 2007/0154563 A1* | 7/2007 | Behnam et al. | 424/549 |
| 2009/0130173 A1 | 5/2009 | Behman et al. | |
| 2009/0191255 A1* | 7/2009 | Vukicevic et al. | 424/423 |
| 2009/0214653 A1 | 8/2009 | Birr et al. | |
| 2009/0317867 A1* | 12/2009 | Luan et al. | 435/69.4 |
| 2011/0104283 A1* | 5/2011 | Mousa et al. | 424/487 |

FOREIGN PATENT DOCUMENTS

| | | |
|---|---|---|
| WO | 89/09788 | 10/1989 |
| WO | 2006125867 | 11/2006 |
| WO | WO 2006/125867 A1 * | 11/2006 |
| WO | 2008/008803 | 1/2008 |
| WO | 2010/090523 | 8/2010 |

OTHER PUBLICATIONS

Tashiro, Efficient Adipocyte and Osteoblast Differentiation from Mouse Induced Pluripotent Stem Cells by Adenoviral Transduction, Stem Cells, 27, pp. 1802-1811, 2009.
Roedel, Factor Seven Activating Protease (FSAP) Can Activate Members of the Transforming Growth Factor (TGF) Family of Growth Factors, Internet Citation, http://www.docstoc.com/docs/75913402/0C-WE-FACTOR-SEVEN-ACTIVATING-PROTEASE-FSAP-INFLAMMATION (2010).
SubName: Full-Bone morphogenetic protein 4, Database Accession No. Q6RF65 (2004).
European Examination Report dated Feb. 2, 2016 for European Application No. 11760215.1.
European Examination Report for European Application No. 11760215.1, dated Dec. 1, 2016, 6 pages.

\* cited by examiner

*Primary Examiner* — Xiaozhen Xie
(74) *Attorney, Agent, or Firm* — RatnerPrestia

(57) ABSTRACT

The invention relates to truncated BMP-4 growth factors and variants thereof. The invention also relates to methods of making and using the truncated BMP-4 growth factors.

25 Claims, 1 Drawing Sheet

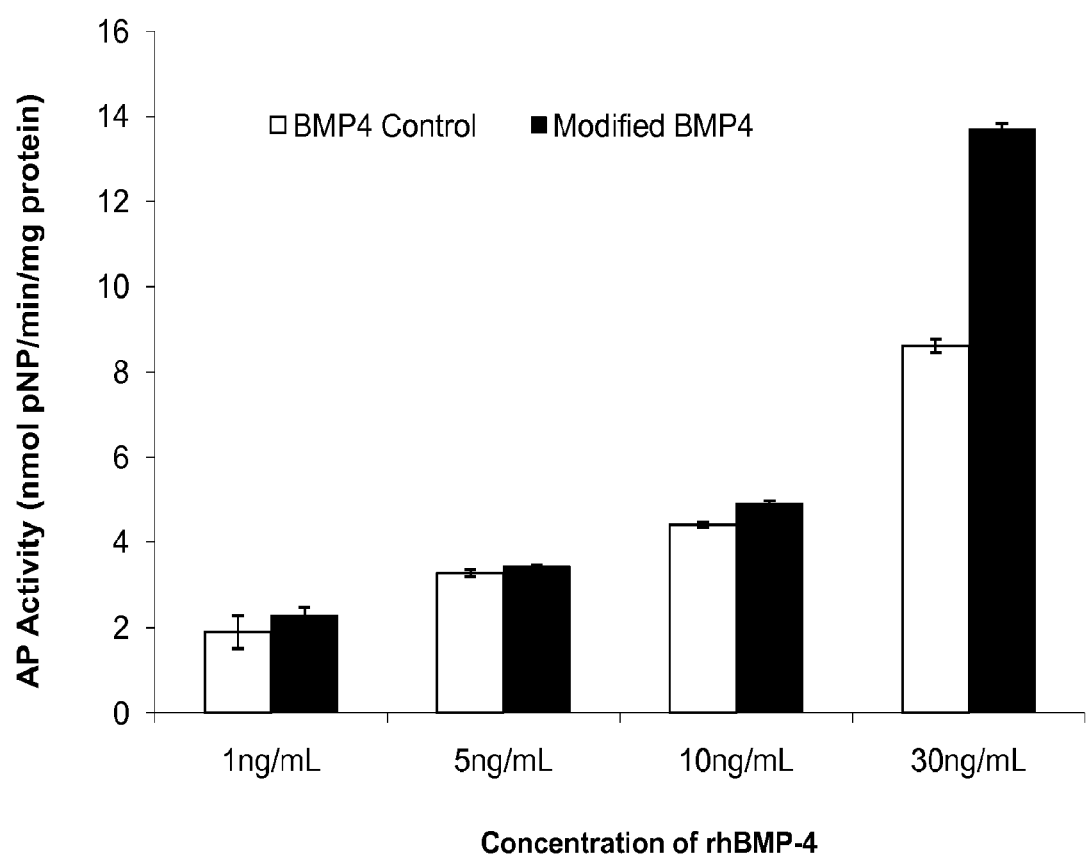

SEQUENCE LISTING

```
<160> NUMBER OF SEQ ID NOS: 7

<210> SEQ ID NO 1
<211> LENGTH: 408
<212> TYPE: PRT
<213> ORGANISM: Homo sapiens

<400> SEQUENCE: 1

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160
```

Phe Arg Glu Gln Val Asp Gln Gly Pro Asp Trp Glu Arg Gly Phe His
                165                 170                 175
Arg Ile Asn Ile Tyr Glu Val Met Lys Pro Ala Glu Val Val Pro
            180                 185                 190
Gly His Leu Ile Thr Arg Leu Leu Asp Thr Arg Leu Val His His Asn
        195                 200                 205
Val Thr Arg Trp Glu Thr Phe Asp Val Ser Pro Ala Val Leu Arg Trp
210                 215                 220
Thr Arg Glu Lys Gln Pro Asn Tyr Gly Leu Ala Ile Glu Val Thr His
225                 230                 235                 240
Leu His Gln Thr Arg Thr His Gln Gly Gln His Val Arg Ile Ser Arg
                245                 250                 255
Ser Leu Pro Gln Gly Ser Gly Asn Trp Ala Gln Leu Arg Pro Leu Leu
            260                 265                 270
Val Thr Phe Gly His Asp Gly Arg Gly His Ala Leu Thr Arg Arg Arg
        275                 280                 285
Arg Ala Lys Arg Ser Pro Lys His His Ser Gln Arg Ala Arg Lys Lys
    290                 295                 300
Asn Lys Asn Cys Arg Arg His Ser Leu Tyr Val Asp Phe Ser Asp Val
305                 310                 315                 320
Gly Trp Asn Asp Trp Ile Val Ala Pro Pro Gly Tyr Gln Ala Phe Tyr
                325                 330                 335
Cys His Gly Asp Cys Pro Phe Pro Leu Ala Asp His Leu Asn Ser Thr
            340                 345                 350
Asn His Ala Ile Val Gln Thr Leu Val Asn Ser Val Asn Ser Ser Ile
        355                 360                 365
Pro Lys Ala Cys Cys Val Pro Thr Glu Leu Ser Ala Ile Ser Met Leu
370                 375                 380
Tyr Leu Asp Glu Tyr Asp Lys Val Val Leu Lys Asn Tyr Gln Glu Met
385                 390                 395                 400
Val Val Glu Gly Cys Gly Cys Arg
                405

<210> SEQ ID NO 2
<211> LENGTH: 106
<212> TYPE: PRT
<213> ORGANISM: Homo sapiens

<400> SEQUENCE: 2

Lys Lys Asn Lys Asn Cys Arg Arg His Ser Leu Tyr Val Asp Phe Ser
1               5                   10                  15
Asp Val Gly Trp Asn Asp Trp Ile Val Ala Pro Pro Gly Tyr Gln Ala
            20                  25                  30
Phe Tyr Cys His Gly Asp Cys Pro Phe Pro Leu Ala Asp His Leu Asn
        35                  40                  45
Ser Thr Asn His Ala Ile Val Gln Thr Leu Val Asn Ser Val Asn Ser
    50                  55                  60
Ser Ile Pro Lys Ala Cys Cys Val Pro Thr Glu Leu Ser Ala Ile Ser
65                  70                  75                  80
Met Leu Tyr Leu Asp Glu Tyr Asp Lys Val Val Leu Lys Asn Tyr Gln
                85                  90                  95
Glu Met Val Val Glu Gly Cys Gly Cys Arg
            100                 105

<210> SEQ ID NO 3

-continued

```
<211> LENGTH: 10
<212> TYPE: PRT
<213> ORGANISM: Artificial
<220> FEATURE:
<223> OTHER INFORMATION: sequence excluded from a second fusion peptide

<400> SEQUENCE: 3

Ser Pro Lys His His Ser Gln Arg Ala Arg
1               5                   10

<210> SEQ ID NO 4
<211> LENGTH: 36
<212> TYPE: PRT
<213> ORGANISM: Artificial
<220> FEATURE:
<223> OTHER INFORMATION: Tat protein basic peptide

<400> SEQUENCE: 4

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 5
<211> LENGTH: 10
<212> TYPE: PRT
<213> ORGANISM: Artificial
<220> FEATURE:
<223> OTHER INFORMATION: Tat protein residues

<400> SEQUENCE: 5

Gly Arg Lys Lys Arg Arg Gln Arg Arg Arg
1               5                   10

<210> SEQ ID NO 6
<211> LENGTH: 318
<212> TYPE: DNA
<213> ORGANISM: Artificial
<220> FEATURE:
<223> OTHER INFORMATION: DNA sequence to code a truncated growth factor

<400> SEQUENCE: 6
aaaaaaaaca aaaactgccg ccgccatagc ctgtatgtgg attttagcga tgtgggctgg      60
aacgattgga ttgtggcgcc gccgggctat caggcgtttt attgccatgg cgattgcccg     120
tttccgctgg cggatcatct gaacagcacc aaccatgcga ttgtgcagac cctggtgaac     180
agcgtgaaca gcagcattcc gaaagcgtgc tgcgtgccga ccgaactgag cgcgattagc     240
atgctgtatc tggatgaata tgataaagtg gtgctgaaaa actatcagga aatggtggtg     300
gaaggctgcg gctgccgc                                                   318

<210> SEQ ID NO 7
<211> LENGTH: 10
<212> TYPE: PRT
<213> ORGANISM: Homo Sapiens

<400> SEQUENCE: 7

Lys Lys Asn Lys Asn Cys Arg Arg His Ser
1               5                   10
```

BMP-4 PEPTIDES AND METHODS OF USE

CROSS-REFERENCE TO RELATED APPLICATIONS

This application is a national phase application of PCT/US2011/029789, filed Mar. 24, 2011, which claims the benefit of U.S. Provisional Application 61/317,075 filed Mar. 24, 2010 which is hereby incorporated by reference in its entirety.

SEQUENCE LISTING SUBMISSION VIA EFS-WEB

A computer readable text file, entitled "067949-5039_SequenceListing.txt," created on or about 20 Sep. 2012, with a file size of about 7 kb contains the sequence listing for this application and is hereby incorporated by reference in its entirety.

BACKGROUND OF THE INVENTION

The invention relates to truncated growth factors and variants thereof. The invention also relates to methods of making and using the truncated growth factors.

SUMMARY OF THE INVENTION

The invention relates to isolated peptides of 115 residues or less, with the peptide comprising an amino acid sequence at least 95% identical to the amino acid sequence of SEQ ID NO: 2.

The invention also relates to fusion proteins comprising the inventive peptides described herein fused to a second peptide, wherein the second peptide comprises an amino acid sequence that is less than 70% identical to the amino acid sequence of SEQ ID NO: 3.

The invention also relates to methods of promoting osteoinductivity or chondroinductivity, with the methods comprising contacting cells with the inventive peptides described herein.

The invention also relates to methods of administering the inventive peptides described herein to matrices.

The invention also relates to methods of increasing osteogenesis or chondrogenesis in cells comprising administering to the cells the inventive peptides described herein.

The invention also relates to methods of increasing a cellular growth factor activity comprising administering to the cells at least one protease and the growth factor comprising SEQ ID NO: 2. In some embodiments, the composition comprises two or more proteases.

BRIEF DESCRIPTION OF THE DRAWINGS

FIG. 1 depicts myoblast expression of alkaline phosphatase after being cultured with modified rhBMP-4. At a concentration of 30 ng/mL, cells treated with modified rhBMP4 expressed significantly higher AP activities than those treated with unmodified mature rhBMP-4.

DETAILED DESCRIPTION OF THE INVENTION

The invention relates to isolated polypeptides. In some embodiments, the isolated polypeptides are 115 amino acid residues or less. The terms "peptide," "polypeptide" and "protein" are used interchangeably herein. As used herein, an "isolated polypeptide" is intended to mean a polypeptide that has been completely or partially removed from its native environment. For example, polypeptides that have been removed or purified from cells are considered isolated. In addition, recombinantly produced polypeptides molecules contained in host cells are considered isolated for the purposes of the present invention. Moreover, a peptide that is found in a cell, tissue or matrix in which it is not normally expressed or found is also considered as "isolated" for the purposes of the present invention. Similarly, polypeptides that have been synthesized are considered to be isolated polypeptides. "Purified," on the other hand is well understood in the art and generally means that the peptides are substantially free of cellular material, cellular components, chemical precursors or other chemicals beyond, perhaps, buffer or solvent. "Substantially free" is not intended to mean that other components beyond the novel peptides are undetectable. The peptides of the present invention may be isolated or purified.

The amino acid sequence of SEQ ID NO: 1 represents the full length "prepropeptide" of bone morphogenetic protein 4 ("BMP-4"). Like most members of the BMP family of peptides, BMP-4 is formed as a full length prepropeptide, which usually contains, from N-terminus to C-terminus, a signal sequence, a propeptide domain and the "mature" peptide. For BMP-4 the signal sequence occurs from amino acid residues 1-19, the propeptide domain is from residues 20 to 292, and the "mature" peptide is from residue 293-408 of SEQ ID NO: 1. The amino acid sequence of hBMP-4 is also available within the UniProt Consortium Database as UniProt Accession No. P12644, the entire record of which is incorporated by reference. Normally, BMP-4, like other members of the BMP family of growth factors is translated into the full length prepropeptide. Through subsequent post-translational processing, the signal peptide and the propeptide domains are cleaved with the remaining portion of the peptide recognized as the "mature" form of the growth factor. After processing, the "mature" form of the protein normally dimerizes and active homodimeric or even heterodimeric bone morphogenetic proteins are secreted from cells and this dimer, in general, binds to its receptor, e.g., BMP receptor type IA (BMPR1A), to initiate the cell signaling cascade typically associated with BMP-4 activity.

The amino acid sequence of SEQ ID NO: 2 represents a novel truncation of the mature BMP-4 and corresponds to amino acid residues 303-408 of SEQ ID NO: 1. As used herein, "modified growth factor" or "truncated growth factor" refers to these novel truncations of any form of BMP-4, including the full length prepropeptide, the propeptide (the full length peptide without the signaling sequence) and the mature form of BMP-4. The invention therefore provides isolated peptides of 115 residues or less, with the peptide comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO: 2. In one specific embodiment, the isolated peptide is 115 residues or less and comprises an amino acid sequence at least 95% identical to the amino acid sequence of SEQ ID NO: 2. In further embodiments, the peptides of the present invention are 115 residues or less and comprises an amino acid sequence 100% identical to the amino acid sequence of SEQ ID NO: 2.

In still further embodiments, the isolated peptide is 115, 114, 113, 112, 111, 110, 109, 108, 107 or 106 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO: 2. In even more embodiments, the peptide variants described herein still retain their ability to specifically interact, at least partially, with its corresponding bone morphogenic protein receptor (BMPR), such as, but not limited to, BMPR type IA (BMPR1A) and, to a lesser extent BMPR type II. In additional embodiments, the peptide variants described herein are functional and capable of promoting osteoinductivity, stimulating proliferation of osteoblasts and/or promoting osteogenesis. In even more embodiments, the modified growth factors of the present invention have enhanced activity compared to the unmodified growth factors. In still even more embodiments, the peptides consist of the amino acid sequence of SEQ ID NO: 2, i.e., 106 amino acids in length and 100% identical to SEQ ID NO: 2.

A polypeptide having an amino acid sequence at least, for example, about 95% "identical" to a reference an amino acid sequence, e.g., SEQ ID NO: 2, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to determine identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine identity and similarity are discussed in Michaels (2011) Current Protocols in Protein Science, Vol. 1, John Wiley & Sons.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment−10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within the reference protein, e.g., wild-type BMP-4, and those positions in the modified BMP-4 that align with the positions on the reference protein. Thus, when the amino acid sequence of a subject BMP-4 is aligned with the amino acid sequence of a reference BMP-4, e.g., SEQ ID NO: 2, the amino acids in the subject sequence that "correspond to" certain enumerated positions of the reference sequence are those that align with these positions of the reference sequence, e.g., SEQ ID NO: 2, but are not necessarily in these exact numerical positions of the reference sequence. Methods for aligning sequences for determining corresponding amino acids between sequences are described herein. Accordingly, the invention provides novel peptides whose sequences correspond to the sequence of SEQ ID NO: 2.

The invention further embraces other species, preferably mammalian, homologs with amino acid sequences that correspond to the modified growth factors of the present invention. Species homologs, sometimes referred to as "orthologs," in general, share at least 35%, 40%, 45%, 50%, 60%, 65%, 70%, 75%, 80%, 85%, 90%, 95%, 96%, 97%, 98%, or 99% sequence identity with the human version of the growth factors. Such corresponding sequences account for the modified growth factor from across a variety of species, such as canine, feline, mouse, rat, rabbit, monkey, etc. of BMP-4. In another embodiment, the invention provides novel peptides whose sequences correspond to the sequence of SEQ ID NO: 2 and retain at least some minimal function.

Modified growth factor products with an additional methionine residue at position −1 ($Met^{-1}$-peptide) are contemplated, as are variants with additional methionine and lysine residues at positions −2 and −1 ($Met^{-2}$-$Lys^{-1}$-peptide). Variants of the modified growth factor with additional Met, Met-Lys, or Lys residues (or one or more basic residues in general) are particularly useful for enhanced recombinant protein production in bacterial host cells.

Variants resulting from insertion of the polynucleotide encoding the modified growth factor into an expression vector system are also contemplated. For example, variants (usually insertions) may arise from when the amino terminus and/or the carboxy terminus of modified growth factor is/are fused to another polypeptide.

In another aspect, the invention provides deletion variants wherein one or more amino acid residues in the modified growth factor peptide are removed. Deletions can be effected at one or both termini of the modified growth factor peptide, or with removal of one or more non-terminal amino acid residues of the modified growth factor peptide. Deletion variants, therefore, include all fragments of the modified growth factor peptide.

Within the confines of the disclosed percent identity, the invention also relates to substitution variants of disclosed polypeptides of the invention. Substitution variants include those polypeptides wherein one or more amino acid residues of truncated growth factor are removed and replaced with alternative residues. In one aspect, the substitutions are conservative in nature; however, the invention embraces substitutions that are also non-conservative. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

Conservative Substitutions

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE II

Conservative Substitutions

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE III

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The polypeptides of the present invention may or may not be involved in a dimer. In one embodiment, the invention provides dimers, wherein the dimers comprise at least one of the novel, modified growth factors described herein. In one specific embodiment, the dimers are homodimers of the novel modified growth factors. In another embodiment, the dimers are heterodimers comprising at least one of the novel modified growth factors. As used herein, a "heterodimer" means a dimer of peptides, wherein the amino acid sequences of the peptides are not 100% identical to each other. Thus, a heterodimer may include a modified growth factor peptide of the present invention dimerized with a normal, "mature" version of the same growth factor.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. In some embodiments, at least one refers, for example, to 1, 2, 3, 4, 5, 6, 7, 8, 9, or 10.

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces modified growth factor peptides that have been covalently modified to include one or more water-soluble polymer attachments such as polyethylene glycol, polyoxyethylene glycol or polypropylene glycol.

Chemically modified growth factor compositions in which the modified growth factor is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g., glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified NgR polymer is destined for therapeutic use, pharmaceutically acceptable polymers will be selected for use.

Pegylation of modified growth factor peptides may be carried out by any of the pegylation reactions known in the art. Preferably, the pegylation is carried out via an acylation reaction or an alkylation reaction with a reactive polyethylene glycol molecule (or an analogous reactive water-soluble polymer). A preferred water-soluble polymer for pegylation of polypeptides is polyethylene glycol (PEG), including, but not limited to bi-functional PEGs. As used herein, "polyethylene glycol" is meant to encompass any of the forms of PEG that have been used to derivatize other proteins, such as mono (C1—C10) alkoxy- or aryloxy-polyethylene glycol.

Chemical derivatization of modified growth factor may be performed under any suitable conditions used to react with a biologically active substance with an activated polymer molecule. Methods for preparing pegylated modified growth factor will generally comprise the steps of (a) reacting the polypeptide with polyethylene glycol, such as a reactive ester or aldehyde derivative of PEG, under conditions whereby modified growth factor polypeptide becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer modified growth factor polypeptides may generally be used to treat conditions that may be alleviated or modulated by administration of the modified growth factor polypeptides described herein. However, the chemically-derivatized polymer: modified growth factor polypeptide molecules disclosed herein may have additional activities, enhanced or reduced biological activity, or other characteristics, such as increased or decreased half-life, as compared to the nonderivatized molecules. The modified growth factor polypeptides, fragments thereof, variants and derivatives, may be employed alone, together, or in combination with other pharmaceutical compositions. For example, cytokines, growth factors, antibiotics, anti-inflammatories and/or chemotherapeutic agents may be co-administered as is appropriate for the indication being treated.

The present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

In one embodiment, the invention provides fusion proteins comprising at least a first and a second fusion peptide. The fusion partners are, generally speaking, covalently bonded to one another via a typical amine bond between the fusion peptides, thus creating one contiguous amino acid chain. In one specific embodiment, the first peptide of the fusion protein comprises a peptide of 115 residues or less, with the peptide comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO: 2. In one specific embodiment, the first fusion peptide is 115 residues or less and comprises an amino acid sequence at least 95% identical to the amino acid sequence of SEQ ID NO: 2. In further embodiments, the first fusion peptide is 115 residues or less and comprises an amino acid sequence 100% identical to the amino acid sequence of SEQ ID NO: 2. In still further embodiments, the first fusion peptide is 114, 113, 112, 111, 110, 109, 108, 107 or 106 residues or less with each first fusion peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO: 2. In even more embodiments, the first fusion peptide consist of the amino acid sequence of SEQ ID NO: 2, i.e., 106 amino acids in length and 100% identical to SEQ ID NO: 2.

In one specific embodiment, the second fusion peptide comprises an amino acid sequence that does not include the amino acid sequence of SEQ ID NO: 3. In more specific embodiments, the second fusion of the present invention comprises an amino acid sequence that is less than 70%, 80%, 90% or 100% identical to SEQ ID NO: 3. The fusion protein of the present invention does not include SEQ ID NO: 1.

Other types of fusion proteins provided by the present invention include but are not limited to, fusions with secretion signals and other heterologous functional regions. Thus, for instance, a region of additional amino acids, particularly charged amino acids, may be added to the N-terminus of the protein to improve stability and persistence in the host cell, during purification or during subsequent handling and storage.

Additional fusion proteins include fusions for enhancing translocation of the protein across cell membranes. For example, Tat is an 86-amino acid protein involved in the replication of human immunodeficiency virus type 1 (HIV-1). The HIV-1 Tat transactivation protein is efficiently taken up by cells, and it has been demonstrated that low concentrations (nM) are sufficient to transactivate a reporter gene expressed from the HIV-1 promoter. Exogenous Tat protein is able to translocate through the plasma membrane and reach the nucleus to transactivate the viral genome. Tat peptide-mediated cellular uptake and nuclear translocation have been demonstrated in several systems. Chemically coupling a Tat-derived peptide (residues 37-72 of Tat) to several proteins results in their internalization in several cell lines or tissues (Fawell (1994) Proc. Natl. Acad. Sci. USA 91, 664-668.

It is well-known that a region of the Tat protein centered on a cluster of basic amino acids is responsible for this translocation activity. A synthetic peptide consisting of the Tat basic amino acids 48-60 with a cysteine residue at the C-terminus coupled to fluorescein maleimide translocates to the cell nucleus as determined by fluorescence microscopy. In addition, a fusion protein (Tat-NLS-β-Gal) consisting of Tat amino acids 48-59 fused by their amino-terminus to β-galactosidase amino acids 9-1023 translocates to the cell nucleus in an ATP-dependent, cytosolic factor-independent manner. Accordingly, the fusion proteins of the present invention may comprise all or a portion of HIV-Tat, such as any sequential residues of the Tat protein basic peptide motif 37-72 (37-CFITKALGISYGRKKRRQRRRPPQG-SQTHQVSLSKQ-72 (SEQ ID NO: 4). The minimum number of amino acid residues can be in the range of from about three to about six. In one embodiment, the Tat portion of the fusion protein is from about three to about five contiguous amino acids in length. In another embodiment, the Tat portion of the fusion protein is about four amino acids in length, i.e., the minimal requirement for one alpha helical turn. In another embodiment, the Tat portion of the fusion protein comprises Tat protein residues 48-57 (GRK-KRRQRRR) (SEQ ID NO: 5).

In additional embodiments of fusion proteins, a region may be added to facilitate purification. For example, "histidine tags" ("his tags") or "lysine tags" (the second fusion peptide) may be appended to the first fusion peptide. Examples of histidine tags include, but are not limited to hexaH, heptaH and hexaHN. Examples of lysine tags include, but are not limited to pentaL, heptaL and FLAG. Such regions may be removed prior to final preparation of the protein. Other examples of a second fusion peptide include, but are not limited to, glutathione S-transferase (GST) and alkaline phosphatase (AP).

The addition of peptide moieties to proteins, whether to engender secretion or excretion, to improve stability and to facilitate purification or translocation, among others, is a familiar and routine technique in the art and may include modifying amino acids at the terminus to accommodate the tags. For example in SEQ ID NO: 2, the N-terminus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins. For example, EP A0464 533 discloses fusion proteins comprising various portions of constant region of immunoglobin molecules together with another human protein or part thereof. In many cases, the Fc part in a fusion protein is thoroughly advantageous for use in therapy and diagnosis and thereby results, for example, in improved pharmacokinetic properties (EP A0232 262). On the other hand, for some uses, it would be desirable to be able to delete the Fc part after the fusion protein has been expressed, detected and purified in the advantageous manner described.

The fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

Fusion proteins of the present invention include, but are not limited to, products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the fusion proteins of the present invention may be glycosylated or may be non-glycosylated. In addition, fusion proteins of the invention may also include an initial modified methionine residue, in some cases as a result of host-mediated processes.

The invention also relates to isolated nucleic acids and to constructs comprising these nucleic acids. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any polypeptide of the invention, including, but not limited to, the fusion proteins of the present invention. For example, the nucleic acids of the invention include polynucleotide sequences that encode glutathione-S-transferase (GST) fusion protein, poly-histidine (e.g., $His_6$), poly-HN, poly-lysine, hemagglutinin, HSV-Tag and at least a portion of HIV-Tat. If desired, the nucleotide sequence of the isolated nucleic acid can include additional non-coding sequences such as non-coding 3' and 5' sequences (including regulatory sequences, for example).

In some embodiments, the isolated nucleic acid of the present invention further relates to the nucleic acids consisting of a nucleic acid sequence at least 95% identical to the nucleic acid sequence of SEQ ID NO: 6. In further embodiments, the invention therefore provides the nucleic acids consisting of a nucleic acid sequence at least about 75%, 80%, 85%, 86%, 87%, 88%, 89%, 90%, 91%, 92%, 93%, 94%, 95%, 96%, 97%, 98%, 99% or 100% identical to the nucleic acid sequence of SEQ ID NO: 6.

The nucleic acid molecules of the invention can be "isolated." As used herein, an "isolated" nucleic acid molecule or nucleotide sequence is intended to mean a nucleic acid molecule or nucleotide sequence that is not flanked by nucleotide sequences normally flanking the gene or nucleotide sequence (as in genomic sequences) and/or has been completely or partially removed from its native environment (e.g., a cell, tissue). For example, nucleic acid molecules that have been removed or purified from cells are considered isolated. In some instances, the isolated material will form part of a composition (for example, a crude extract containing other substances), buffer system or reagent mix. In other circumstances, the material may be purified to near homogeneity, for example as determined by PAGE or column chromatography such as HPLC. Thus, an isolated nucleic acid molecule or nucleotide sequence can includes a nucleic acid molecule or nucleotide sequence which is synthesized chemically, using recombinant DNA technology or using any other suitable method. To be clear, a nucleic acid contained in a vector would be included in the definition of "isolated" as used herein. Also, isolated nucleotide sequences include recombinant nucleic acid molecules (e.g., DNA, RNA) in heterologous organisms, as well as partially or substantially purified nucleic acids in solution. "Purified," on the other hand is well understood in the art and generally means that the nucleic acid molecules are substantially free of cellular material, cellular components, chemical precursors or other chemicals beyond, perhaps, buffer or solvent. "Substantially free" is not intended to mean that other components beyond the novel nucleic acid molecules are undetectable. The nucleic acid molecules of the present invention may be isolated or purified. Both in vivo and in vitro RNA transcripts of a DNA molecule of the present invention are also encompassed by "isolated" nucleotide sequences.

The invention also encompasses variations of the nucleotide sequences of the invention, such as those encoding functional fragments or variants of the polypeptides as described above. Such variants can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions.

The invention described herein also relates to fragments of the isolated nucleic acid molecules described herein. The term "fragment" is intended to encompass a portion of a nucleotide sequence described herein which is from at least about 20 contiguous nucleotides to at least about 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g., nucleic acid molecules which specifically hybridize to a nucleotide sequence encoding polypeptides described herein and encode a modified growth factor). Hybridization probes include synthetic oligonucleotides which bind in a base-specific manner to a complementary strand of nucleic acid.

Such nucleic acid molecules can be detected and/or isolated by specific hybridization e.g., under high stringency conditions. "Stringency conditions" for hybridization is a term of art that refers to the incubation and wash conditions, e.g., conditions of temperature and buffer concentration, which permit hybridization of a particular nucleic acid to a second nucleic acid; the first nucleic acid may be perfectly complementary, i.e., 100%, to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology, John Wiley & Sons). The exact conditions which determine the stringency of hybridization depend not only on ionic strength, e.g., 0.2×SSC, 0.1×SSC of the wash buffers, temperature, e.g., room temperature, 42° C., 68° C., etc., and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined. Exemplary conditions are described in Krause (1991) Methods in Enzymology, 200:546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g., high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example. The term "primer" is used herein as it is in the art and refers to a single-stranded oligonucleotide which acts as a point of initiation of template-directed DNA synthesis under appropriate conditions in an appropriate buffer and at a suitable temperature. The appropriate length of a primer depends on the intended use of the primer, but typically ranges from about 15 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The present invention also relates to vectors that include nucleic acid molecules of the present invention, host cells that are genetically engineered with vectors of the invention and the production of proteins of the invention by recombinant techniques.

In accordance with this aspect of the invention, the vector may be, for example, a plasmid vector, a single- or double-stranded phage vector, or a single- or double-stranded RNA or DNA viral vector. Such vectors may be introduced into cells as polynucleotides, for example DNA, by well-known techniques for introducing DNA and RNA into cells. Viral vectors may be replication competent or replication defective. In the latter, case viral propagation generally will occur only in complementing host cells.

In certain respects, the vectors to be used are those for expression of polynucleotides and proteins of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or proteins in a host may be used for expression in this regard.

The DNA sequence in the expression vector is operatively linked to appropriate expression control sequence(s) including, for instance, a promoter to direct mRNA transcription. Representatives of such promoters include, but are not limited to, the phage lambda PL promoter, the *E. coli* lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing *E. coli* and other bacteria.

The vector containing the appropriate DNA sequence, as well as an appropriate promoter, and other appropriate control sequences, may be introduced into an appropriate host using a variety of well-known techniques suitable to expression therein of a desired polypeptide. Representative examples of appropriate hosts include bacterial cells, such as, but not limited to, *E. coli, Streptomyces, Bacillus,* and *Salmonella* cells; fungal cells, such as yeast cells; insect cells such as *Drosophila* S2 and *Spodoptera* Sf9 cells; animal cells such as CHO, COS and Bowes melanoma cells; and plant cells. Hosts for of a great variety of expression constructs are well known, and those of skill in the art will be enabled by the present disclosure to select an appropriate host for expressing one of the proteins of the present invention.

Examples of vectors that may be useful for fusion proteins include, but are not limited to, pGEX (Pharmacia), pMAL (New England Biolabs) and pRIT5 (Pharmacia) that fuse glutathione-S-transferase (GST), maltose E binding protein, or protein A, respectively, to the target recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Examples of vectors for expression in yeast *S. cerevisiae* include pYepSec1 (Baldari (1987) EMBO J. 6, 229-234), pMFa (Kurjan (1982) Cell 30, 933-943), pJRY88 (Schultz (1987) Gene 54, 115-123), pYES2 (Invitrogen) and picZ (Invitrogen).

Alternatively, the modified growth factors can be expressed in insect cells using baculovirus expression vectors. Baculovirus vectors available for expression of proteins in cultured insect cells (e.g., SF9 cells) include the pAc series (Smith (1983) Mol. Cell. Biol. 3, 2156 2165) and the pVL series (Lucklow (1989) Virology 170, 31-39).

In yet another embodiment, a nucleic acid of the invention is expressed in mammalian cells using a mammalian expression vector. Examples of mammalian expression vectors include pCDM8 (Seed (1987) Nature 329, 840) and pMT2PC (Kaufman (1987) EMBO J. 6, 187 195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see Sambrook (2010) Molecular Cloning: A Laboratory Manual. Cold Spring Harbor Laboratory Press.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include liver-specific promoters (e.g., albumin promoter), lymphoid-specific promoters such as, but not limited to, T cell receptors and immunoglobulins, neuron-specific promoters (e.g., neurofilament promoter), pancreas-specific promoters, mammary gland-specific promoters (e.g., milk whey promoter), bone-specific promoters (e.g., osteocalcin, osteopontin or bone sialoprotein, promoter regions), cartilage specific promoters (e.g., WARP) and muscle specific promoters (Desmin, myglobin, etc) just to name a few. Developmentally-regulated promoters are also encompassed, e.g., the murine hox promoters (Kessel and Gruss (1990) Science 249, 374 379) and the α-fetoprotein promoter (Campes and Tilghman (1989) Genes Dev. 3, 537 546).

The present invention also relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. The host cell can be stably or transiently transfected with the construct. The polynucleotides may be introduced alone or with other polynucleotides. Such other polynucleotides may be introduced independently, co-introduced or introduced joined to the polynucleotides of the invention. As used herein, a "host cell" is a cell that normally does not contain any of the nucleotides of the present invention and contains at least one copy of the nucleotides of the present invention. Thus, a host cell as used herein can be a cell in a culture setting or the host cell can be in an organism setting where the host cell is part of an organism, organ or tissue.

Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Pseudomonas, Staphylococcus*, and *Streptomyces*.

If a eukaryotic expression vector is employed, then the appropriate host cell would be any eukaryotic cell capable of expressing the cloned sequence. In one embodiment, eukaryotic cells are cells of higher eukaryotes. Suitable eukaryotic cells include, but are not limited to, non-human mammalian tissue culture cells and human tissue culture cells. Other host cells include, but are not limited to, insect cells, HeLa cells, Chinese hamster ovary cells (CHO cells), African green monkey kidney cells (COS cells), human 293 cells, and murine 3T3 fibroblasts.

In addition, a yeast cell may be employed as a host cell. Yeast cells include, but are not limited to, the genera *Saccharomyces, Pichia* and *Kluveromyces*. In one embodiment, the yeast hosts are *S. cerevisiae* or *P. pastoris*. Yeast vectors may contain an origin of replication sequence from a 2T yeast plasmid, an autonomously replication sequence (ARS), a promoter region, sequences for polyadenylation, sequences for transcription termination and a selectable marker gene. Shuttle vectors for replication in both yeast and *E. coli* are also included herein.

Introduction of a construct into the host cell can be affected by calcium phosphate transfection, DEAE-dextran mediated transfection, cationic lipid-mediated transfection, electroporation, transduction, infection or other methods.

For stable transfection of mammalian cells, it is known that, depending upon the expression vector and transfection technique used, only a small fraction of cells may integrate the foreign DNA into their genome. To identify and select these integrants, a gene that encodes a selectable marker (e.g., resistance to antibiotics) is generally introduced into the host cells along with the gene of interest. Various selectable markers include those that confer resistance to drugs, such as G418, hygromycin, dihydrofolate reductase (DHFR) and methotrexate. Nucleic acid encoding a selectable marker can be introduced into a host cell on the same vector as that encoding modified growth factor or can be introduced on a separate vector. Cells stably transfected with the introduced nucleic acid can be identified by drug selection (e.g., cells that have incorporated the selectable marker gene will survive, while the other cells die). In one embodiment, the polypeptides of the invention are expressed in Chinese Hamster Ovary (CHO) cells.

The modified growth factor expression vectors prepared as above are introduced into CHO cells by any known method, including, but not limited to the calcium phosphate method and electroporation.

Transformants carrying the expression vectors are selected based on the above-mentioned selectable markers. Repeated clonal selection of the transformants using the selectable markers allows selection of stable cell lines expressing the modified growth factor constructs. Increased concentrations in the selection medium allows gene amplification and greater expression of the desired modified growth factor. The host cells, for example CHO cells, containing the recombinant modified growth factor can be produced by cultivating the CHO cells containing the modified growth factor expression vectors constitutively expressing the modified growth factor constructs.

Accordingly, the current invention also relates to methods of producing a modified growth factor comprising culturing the host cells of the invention under conditions such that the modified growth factor is expressed, and recovering said protein. The culture conditions required to express the proteins of the current invention are dependent upon the host cells that are harboring the polynucleotides of the current invention. The culture conditions for each cell type are well-known in the art and can be easily optimized, if necessary. For example, a nucleic acid encoding a polypeptide of the invention, or a construct comprising such nucleic acid, can be introduced into a suitable host cell by a method appropriate to the host cell selected, e.g., transformation, transfection, electroporation, infection, such that the nucleic acid is operably linked to one or more expression control elements as described herein. Host cells can be maintained under conditions suitable for expression in vitro or in vivo, whereby the encoded polypeptide is produced. For example host cells may be maintained in the presence of an inducer, suitable media supplemented with appropriate salts, growth factors, antibiotic, nutritional supplements, etc., which may facilitate protein expression. In additional embodiments, the modified growth factors of the invention can be produced by in vitro translation of a nucleic acid that encodes the modified growth factor, by chemical synthesis or by any other suitable method. If desired, the modified growth factor can be isolated from the host cell or other environment in which the protein is produced or secreted. It should therefore be appreciated that the methods of producing the modified growth factors encompass expression of the polypeptides in a host cell of a transgenic animal or plant. See U.S. Pat. Nos. 6,013,857, 5,990,385, and 5,994,616.

In situations where the modified BMP-4 will be found primarily intracellularly, intracellular material (including inclusion bodies for Gram-negative bacteria) can be extracted from the host cell using any standard technique known to one of ordinary skill in the art. Such methods would encompass, by way of example and not by way of limitation, lysing the host cells to release the contents of the periplasm/cytoplasm by French press, homogenization and/or sonication followed by centrifugation.

If the modified BMP-4 has formed inclusion bodies in the cytosol, such inclusion bodies may frequently bind to the inner and/or outer cellular membranes. Upon centrifugation, the inclusion bodies will be found primarily in the pellet material. The pellet material can then be treated at pH extremes or with one or more chaotropic agents such as a detergent, guanidine, guanidine derivatives, urea, or urea derivatives in the presence of a reducing agent such as dithiothreitol at alkaline pH or tris-carboxyethyl phosphine at acid pH to release, break apart and solubilize the inclusion bodies. Once solubilized, the modified growth factor peptide can be analyzed using gel electrophoresis, immunoprecipitation or the like. Various methods of isolating the modified growth factor peptide would be apparent to one of ordinary skill in the art, for example, isolation may be accomplished using standard methods such as those set forth below and in Marston et al (1990) Meth. Enzymol. 182, 264-275.

If the modified growth factor peptide is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a certain pH, usually above 7, and in the presence of a particular concentration of a chaotrope. The selection of chaotrope is very similar to the choices used for inclusion body solubilization, but usually at a lower concentration, and is not necessarily the same chaotrope as used for the solubilization. It may be required to employ a reducing agent or the reducing agent plus its oxidized form in a specific ratio, to generate a particular redox potential allowing for disulfide shuffling during the formation of the protein's cysteine bridge(s). Some of the commonly used redox couples include cysteine/cysteine, glutathione (GSH)/dithiobis GSH, cupric chloride, dithiothreitol (DTT)/dithiane DTT, 2-mercaptoethanol (bME)/dithio-b(ME). To increase the efficiency of the refolding, it may be necessary to employ a cosolvent, such as glycerol, polyethylene glycol of various molecular weights and arginine.

Other methods of preparing the modified growth factors of the present invention include, but are not limited to, contacting a form of BMP-4 with a protease. In one embodiment, the methods comprise contacting the mature form of BMP-4 with a protease to produce the modified growth factors of the present invention. In one embodiment, the protease is a serine protease, a threonine protease, a metalloproteinase, a cysteine protease, an aspartate protease or a glutamic acid protease. Examples of such proteases are well known in the art and include proteases from both eukaryotic and prokaryotic sources. Examples of serine proteases include, but are not limited to, chymotrypsin, trypsin, elastase, subtilisin and alpha/beta hydrolases. Examples of cysteine proteases include, but are not limited to, actinidain, bromelain, calpains, some cathepsins, clostripain and papain. Examples of aspartate proteases include, but are not limited to, some cathepsins, chyomsin, renin, pepsin and HIV-1 protease. Examples of metalloproteinases include, but are not limited to, the matrix metalloproteinase (MMP) family of proteases that include MMP-1, MMP-2, MMP-3, MMP-4, MMP-5, MMP-6, MMP-7, MMP-8, MMP-9, MMP-10, MMP-11, MMP-12, MMP-13, MMP-14, MMP-15, MMP-16, MMP-17, MMP-18 and membrane-type MMP (MT-MMP), to name a few. Many of these MMPs are known by other names in the art and one of skill will be informed of synonyms of the various enzymes. For example, some of the "collagenases" are MMP-1, MMP-8, MMP-13, MMP-14, MMP-18 and dispases, and some of the "gelatinases" are MMP-2, MMP-9 and MMP-12; some of the "stromelysins" are MMP-3, MMP-10 and MMP-11, and some of the membrane-type matrix metalloproteinases are MMP-14, MMP-15, MMP-16, MMP-17, MMP-24, and MMP-25. Collagenases are examples of metalloproteinases that break down native collagen or gelatin. A variety of microorganisms and many different types of animal cells produce collagenases. Bacterial collagenases are often used in the laboratory to digest tissues and isolate individual cells. Collagenase produced by *Clostridium histolyticum* (*C. histolyticum*) is a zinc metalloproteinase that degrades various types of collagen and gelatin. Additional examples of metalloproteinases are the astacin family, such as, but not limited to, astacin, tolloid, xolloid, mammalian tolloid like (mTLL), BMP-1, meprin A and B, and matrilysin and the aggrecanase (ADAMTS) family of metalloproteinase, such as, but not limited to, ADAMTS-1, ADAMTS-2, ADAMTS-3, ADAMTS-4, ADAMTS-5.

Of course, the methods include contacting a form of BMP-4 with more than one protease either sequentially or simultaneously. In addition, the proteases used herein can be recombinant or isolated from various sources. The proteases used herein need not be isolated from the same cellular or animal source as the mature form of the BMP-4. For example, many proteases are found only in prokaryotes, yet these proteases are functional against proteins from eukaryotes. Factors affecting enzyme activity include, but are not limited to, salt concentrations of buffer, pH and temperature. One of skill in the art will readily understand the conditions necessary to promote peptide cleave based upon the enzyme used.

In some embodiments, the ratio of the amount of protease(s) to the amount of growth factor(s) may be between about 1 mol protease:1000 mol growth factor and about 1000 mol:1 mol, between about 1 mol protease:100 mol growth factor and about 1000 mol:1 mol, between about 1 mol:10 mol and about 1000 mol:1 mol, between about 1 mol:10 mol and about 100 mol:1 mol, between about 1 mol:10 mol and about 10 mol:1 mol, or between about 1 mol:1 mol and about 10 mol:1 mol. In further embodiments, the ratio of the amount of collagenase(s) to the amount of growth factor(s) may be between about 1 mol collagenase:100 mol growth factor and about 1000 mol:1 mol, between about 1 mol:10 mol and about 1000 mol:1 mol, between about 1 mol:10 mol and about 100 mol:1 mol, or between about 1 mol:1 mol and about 10 mol:1 mol. The ratio of the amount of trypsin to the amount of growth factor(s) may be between about 1 mol trypsin: 1000 mol growth factor and about 1000 mol:1 mol, between about 1 mol:100 mol and about 1000 mol:1 mol, between about 1 mol:10 mol and about 100 mol:1 mol, or between about 1 mol:10 mol and about 10 mol:1 mol. The ratio of the amount of clostripain to the amount of growth factor(s) may be between about 1 mol clostripain:1000 mol growth factor and about 1000 mol:1 mol, between about 1 mol:100 mol and about 1000 mol:1 mol, between about 1 mol:10 mol and about 100 mol:1 mol, or between about 1 mol:1 mol and about 10 mol:1 mol. The ratio of the amount of dispase to the amount of growth factor(s) may be between about 1 mol dispase: 1000 mol growth factor and about 1000 mol:1 mol, between about 1 mol:100 mol and about 1000 mol:1 mol, between about 1 mol:10 mol and about 100 mol:1 mol, or between about 1 mol:10 mol and about 10 mol:1 mol.

The treatment of growth factor(s) with proteases may be performed at a temperature between about 0° C. and about 40° C., about 4° C. and about 40° C., or at about 37° C. or lower, in some embodiments. A growth factor may be treated with collagenase for between about 30 minutes and 3 days, about 1 hour and about 48 hours, about 2 hours and about 48 hours, or about 2 hours and about 24 hours, in certain embodiments. A growth factor may be treated with trypsin or clostripain for between about 5 minutes and 3 days, about 15 minutes and about 48 hours, about 15 minutes and about 24 hours, or about 30 minutes and about 18 hours. A growth factor may be treated with dispase for between about 5 minutes and 2 days, about 15 minutes and about 24 hours, about 15 minutes and about 18 hours, or about 15 minutes and about 8 hours. All these conditions do not count the extra protein or peptide substrate in the treatment mixture. Treatment may include mixing and/or incubation. Incubation may be performed under static or dynamic conditions, such as with agitation, shaking, stirring, mixing, horizontal motion, rocking, and others.

In some embodiments, the protease may be a recombinant protein or peptide fragment, a chemically synthesized protein or peptide fragment, or it may be extracted from a natural source and, optionally, modified, for example by being cleaved, heat-inactivated, chemically-modified, or other methods. In other embodiments, certain aspects of the enzymatic activity of a protease may be inhibited or altered, and the protease having altered activity may be added to one or more growth factors to change the biological activity of the growth factor.

In additional embodiments, the activity of a protease may be modulated before, during, or after treatment of at least one growth factor with the protease. For example, the protease activity of a collagenase may be significantly reduced before it is used to treat a growth factor. In another example, the activity of a protease may be modulated before, during, or after administering to cells. In certain embodiments, the activity of a protease may be modulated by methods comprising heat inactivation, radiation inactivation, protease substrate neutralization, or chemical inhibition, among others. The chemical inhibitor used to modulate the activity of metalloproteinases may be selected from metal chelating agents, such as EDTA; cysteine and serine protease inhibitors, such as N-ethylmaleimide, phenylmethylsulfonyl fluoride (PMSF), and leupeptin; classical metalloproteinase inhibitor, such as phosphoramidon, and bestatin; general protein inhibitor, such as α2-macroglobuli, or natural or synthetic tissue inhibitors of metalloproteinases (TIMPs), such as TIMP-1, TIMP-2, TIMP-3, TIMP-4; and other inhibitors.

The form of BMP-4 used in these methods can also be recombinant or can be isolated from a variety of cellular or animal sources. In one embodiment of the present invention, the BMP-4, in any form, that is contacted with the at least one protease is a recombinant BMP-4. In one specific embodiment, the recombinant BMP-4 is contacted with a metalloproteinase to generate the novel, truncated BMP-4 peptides of the present invention. In a more specific embodiment, the recombinant BMP-4 is contacted with a collagenase to generate the novel, truncated BMP-4 peptides of the present invention. In an even more specific embodiment, the recombinant BMP-4 that is contacted with a collagenase is a recombinant mature form of BMP-4. In a still more specific embodiment, recombinant mature BMP-4 is contacted with a collagenase and/or clostripain to generate the novel, truncated BMP-4 peptides of the present invention. In another specific embodiment, recombinant mature BMP-4 is contacted with a trypsin or dispase to generate the novel, truncated BMP-4 peptides of the present invention.

Once treated with at least one protease, in some embodiments, the resulting peptides are isolated and purified using routine methods in the art. Examples of purification methods include, but are not limited to size exclusion chromatography, high-performance liquid chromatography, ion exchange chromatography, electrophoresis, Western blotting and subsequent processing of the membrane. In one embodiment of the present invention, the resulting peptide that is purified after protease treatment comprises the amino acid sequence of SEQ ID NO: 2. In other embodiments, after being treated with a protease, the resulting peptides are not isolated or purified and are administered to a cell in the presence of the protease. In another embodiment, the resulting peptide is isolated or purified and then is administered to a cell with a protease. In again another embodiment, after being treated with a protease, without being isolated or purified, the resulting peptides are administered to a cell in the presence of the protease, then another protease is administered together.

The modified growth factor peptides of the present invention may also be prepared by synthetic methods using solid-phase synthetic techniques. The synthesized polypeptides may be re-natured into correct folding pattern under appropriate conditions and bioactive dimmers can be induced from monomers using appropriate buffers and conditions. The correctly folded dimers may be further separated from monomers using appropriate column to increase the yield of functional bioactive factors.

Regardless of method of preparation, be it recombinantly, enzymatically or synthetically, the novel modified growth factors, as monomers or dimers, can be prepared as a composition. In one embodiment, the composition is a pharmaceutical composition. For example, one or more cofactors may be added to the truncated mature bioactive factor of the present invention to form a composition. Cofactors that may be added include, but are not limited to, heparin, hyaluronic acid, a fibronectin, an elastin, a laminin, albumin, a proteoglycan, collagen, gelatin, a divalent cation, calcium chloride, zinc sulfate, magnesium chloride, sodium bicarbonate, sodium chloride, sodium acetate, or sodium phosphate. In some embodiments, a protein or a protein fragment may be added as a cofactor to the modified growth factor peptides of the present invention.

The compositions, or pharmaceutical compositions, comprising the nucleic acid molecules or polypeptides typically comprise the nucleic acid molecule or protein and a pharmaceutically acceptable carrier. As used herein, "pharmaceutically acceptable carrier" or "pharmaceutical carrier" is intended to include any and all solvents, dispersion media, coatings, antibacterial and antifungal agents, isotonic and absorption delaying agents, and the like, compatible with pharmaceutical administration. The nature of the pharmaceutical carrier or other ingredients will depend on the specific route of administration and particular embodiment of the invention to be administered. Examples of techniques and protocols that are useful in this context are, inter alia, found in Remington: The Science and Practice of Pharmacy (2010), Lippincott, Williams & Wilkins. Examples of such pharmaceutical carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include, but are not limited to, a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable pharmaceutical carriers include physiological saline, bacteriostatic water, Cremophor EL™ (BASF) or phosphate buffered saline (PBS). In all cases, the compositions must be sterile and should be fluid to the extent that easy syringeability exists. It must be stable under the conditions of manufacture and storage and must be preserved against the contaminating action of microorganisms such as bacteria and fungi. The pharmaceutical carrier can be a solvent or dispersion medium containing, for example, water, ethanol, polyol (for example, glycerol, propylene glycol and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the modified growth factor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutical carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid pharmaceutical carrier for use as a mouthwash, wherein the compound in the fluid pharmaceutical carrier is applied orally and swished and expectorated or swallowed. Pharmaceutically compatible binding agents, and/or adjuvant materials can be included as part of the composition. The tablets, pills, capsules, troches and the like may contain any of the following ingredients, or compounds of a similar nature, such as but not limited to a binder, such as microcrystalline cellulose, gum tragacanth or gelatin, an excipient such as starch or lactose, a disintegrating agent such as alginic acid, Primogel or corn starch, a lubricant such as magnesium stearate or Sterotes, a glidant such as colloidal silicon dioxide, a sweetening agent such as sucrose or saccharin, or a flavoring agent such as peppermint, methyl salicylate or orange flavoring.

In one embodiment, the active compounds are prepared with pharmaceutical carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These compositions can be prepared according to methods known to those skilled in the art, for example, as described in U.S. Pat. No. 4,522,811. It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack or dispenser together with instructions for administration.

The dosage of BMP-4 peptides will depend on the disease state or condition to be treated and other clinical factors such as weight and condition of the human or animal and the route of administration of the compound. For treating human or animals, between approximately 0.005 mg/kg of body weight to 500 mg/kg of body weight of the compound can be administered. Therapy is typically administered at lower dosages and is continued until the desired therapeutic outcome is observed.

Methods of determining the dosages of compounds to be administered to a patient and modes of administering compounds to an organism are disclosed in, for example, WO 96/22976. Those skilled in the art will appreciate that such descriptions are applicable to the present invention and can be easily adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

The invention also relates to methods of altering intracellular signaling of a cell, comprising contacting the cells with at least one of the peptides of the present invention, wherein the cell possesses a receptor that specifically binds to the modified growth factors of the present invention. The peptides utilized in the methods can be in monomeric, homodimeric or heterodimeric form. The specific binding of the modified growth factors to its receptor will, in turn, initiate the intracellular signaling cascade that is normally associated with the unmodified forms of the growth factor. For example, the "mature" form of BMP-4 normally binds to its type I and/or type II receptors, such as BMPR1A. The receptor phosphorylates cytoplasmic targets that include the Smad family of proteins. Smads are a class of proteins that function as intracellular signaling effectors for the TGF-β superfamily of secreted polypeptides. The activated BMP type I receptors will phosphorylate Smad1, Smad 5, and/or Smad 8. Phosphorylated Smad 1, 5, and 8 proteins, in turn, form a complex with Smad 4 and then translocate into the nucleus and interact with the transcription factors that regulate the expression of target genes.

Accordingly, the present invention provides methods of stimulating phosphorylation of Smad 1, Smad 5 and/or Smad 8 in a cell comprising contacting the cell(s) with at least one modified growth factor of the invention. The peptides utilized in the methods can be in monomeric, homodimeric or heterodimeric form. The activity of the novel peptides with respect to phosphorylating the Smad proteins may or may not be altered relative to the normal, mature growth factor. For example, the novel modified growth factors may increase or decrease phosphorylation of Smad 1, 5 and/or 8 compared to receptor binding of normal, mature growth factor. As another example, the novel modified growth factors may bind tighter or looser to its receptor (lower Kd) compared to receptor binding of normal, mature growth factor. One of skill in the art can readily determine if a particular protein is more or less phosphoylated over control groups using well known techniques such as transcription of reporter genes, ELISA assays, etc. Additional methods of the present invention comprise assessing the levels of Smad phosphorylation, for example, Smad 1, Smad 5 or Smad 8, both before and after contacting the cell(s) with the novel peptides of the present invention and determining the increase or decrease of Smad phosphorylation in response to the novel peptides of the present invention.

In another embodiment, the present invention provides methods of stimulating promoter activity in a cell or population of cells, where the promoter is responsive to activated Smad complexes, with the methods comprising contacting the cell(s) with at least one modified growth factor peptide of the present invention. The peptides utilized in the methods can be in monomeric, homodimeric or heterodimeric form. One of skill in the art would be aware of promoters that respond to activated Smad complexes. See, for example, Massague (2000) Cell, 103:295-309. The activity of the novel peptides with respect to stimulating Smad-responsive promoters may or may not be altered relative to the normal, mature growth factor. For example, the novel modified growth factors may increase or decrease activation of Smad-responsive promoters compared to receptor binding of normal, mature growth factor. One of skill in the art can readily determine if a promoter is more or less activated over control groups using well known techniques such as transcription of reporter genes, ELISA assays, etc. Additional methods of the present invention comprise assessing the activity of a Smad-responsive promoter both before and after contacting the cell(s) with the novel peptides of the present invention and determining the increase or decrease of the promoter in response to the novel peptides of the present invention.

As used herein, "contacting," when used in connection with the methods of the present invention means bringing the novel peptides, in monomeric, homodimeric or heterodimeric form, in proximity to the target cells such that a specific binding event or a biological effect is possible. Thus, contacting can include adding the novel peptides in culture medium and applying the culture medium to cells in culture. Contacting also encompasses transfecting a cell with at least one vector described herein and allowing the cell to produce the modified growth factor. Of course, contacting would also include administration of the modified growth factor peptides, or pharmaceutical compositions thereof, of the present invention to cells in an intact organism. Compositions for administering the novel peptides of the present invention have been described herein.

As used herein, "administering," and "administer" are used to mean introducing at least one compound comprising at least one novel modified growth factor peptide into a subject. The peptides utilized in the administration methods can be in monomeric, homodimeric or heterodimeric form. When administration is for the purpose of treatment, the substance is provided at, or after the onset of, a symptom or condition in need of treatment. The therapeutic administration of this substance serves to attenuate any symptom, or prevent additional symptoms from arising. When administration is for the purposes of preventing a condition from arising ("prophylactic administration"), the substance is provided in advance of any visible or detectable symptom. The prophylactic administration of the substance serves to attenuate subsequently arising symptoms or prevent symptoms from arising altogether. The route of administration of the compound includes, but is not limited to, topical, transdermal, intranasal, vaginal, rectal, oral, subcutaneous intravenous, intraarterial, intramuscular, intraosseous, intraperitoneal, epidural and intrathecal as previously disclosed herein.

Furthermore, the methods would also include coadministering one or more substances in addition to the novel peptides of the present invention. The term "coadminister" indicates that each of at least two compounds is administered during a time frame wherein the respective periods of biological activity or effects overlap. Thus the term includes sequential as well as coextensive administration of the compounds of the present invention. And similar to administering compounds, coadministration of more than one substance can be for therapeutic and/or prophylactic purposes. If more than one substance is coadministered, the routes of administration of the two or more substances need not be the same.

The invention also relates to methods of promoting osteoinductivity, with the methods comprising contacting cells with at least one modified growth factor peptide of the present invention or compositions described herein. As used herein, "osteoinductivity" can refer to causing cells to differentiate into cells that are more osteoblast-like in phenotype, or the term can refer to increasing the proliferation of osteoblasts, or both. The cells, prior to contact with the modified growth factor peptide(s) of the present invention, may be undifferentiated or partially differentiated cells. The cells may be present in culture or in a tissue, organ or portion thereof or in an organism. The osteoinductive activity of the novel peptides may or may not be altered, including but not limited to, enhanced activity, relative to the normal, mature growth factor.

The invention also relates to methods of promoting chondroinductivity, with the methods comprising contacting cells with at least one modified growth factor peptide of the present invention or compositions described herein. As used herein, "chondroinductivity" can refer to causing cells to differentiate into cells that are more chondrocyte-like in phenotype, or the term can refer to increasing the proliferation of chondrocytes, or both. The cells, prior to contact with the modified growth factor peptide(s) of the present invention, may be undifferentiated or partially differentiated cells. The cells may be present in culture or in a tissue, organ or portion thereof or in an organism. The chondroinductive activity of the novel peptides may or may not be altered, including but not limited to, enhanced activity, relative to the normal, mature growth factor.

For example, the invention provides for growing and/or culturing cells in the presence of one or more modified growth factor peptides or compositions described herein. "Growing and/or culturing cells in the presence of" includes traditional cell culture methods as well a placing cells in the presence of the modified growth factors in any setting, such as in natural or synthetic matrices or tissues. The cells may be mammalian, such as but not limited to human, bovine, porcine, murine, ovine, equine, canine, feline and others. In some embodiments, the cells may be mesenchymal stem cells, such as adipose-derived stem cells, embryonic stem cells, progenitor cells, differentiated cells, undifferentiated cells, and/or induced pluripotent stem cells. Appropriate cells may also include, but are not limited to cells of the ectodermal lineage, cells of the mesodermal lineage, and cells of the endodermal lineage. Examples of cells of the ectodermal lineage include but are not limited to keratinocytes, osteoblasts, chondrocytes, neurons. Examples of cells of the mesodermal lineage include but are not limited to myoblasts, adipocytes, fibroblasts, endothelial cells, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines. The cells to which the modified growth factor peptides have been administered may be placed directly into a tissue, organism or other setting such as a matrix, including, but not limited to, bone matrices.

In some embodiments, the cells may be derived from autologous or allogeneic sources. The cells may be differentiated cells including chondrocytes, osteoblasts, osteoclasts, endothelial cells, epithelial cells, fibroblasts, and periosteal cells. Additionally, the cells may be totipotent, pluripotent, multipotent, progenitor, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, muscle. The stem cells may be derived from skeletal muscle, smooth muscle, and cardiac muscle. The stem cells may be derived from genetic reprogramming of mature cells, such as induced pluripotent stem cells (iPSCs).

Any cell described herewith may be cultured with one or more modified growth factors or compositions described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the presence of one or more modified growth factors and (1) a tissue or an organ, (2) a matrix, or (3) a combination thereof. Cells that have been cultured in the presence of one or more modified growth factors in a cell culture medium may subsequently be applied to a matrix, a tissue, an organ or a combination thereof, in certain embodiments.

In some embodiments, treated cells are cryopreserved. Cryopreservation agents may be used to preserve treated cells, in certain embodiments. In some embodiments, treated cells are seeded onto a matrix, and the cell-seeded matrix may be preserved using at least one cryopreservation agent. At least one cofactor may be added to treated cells, in some embodiments. Cofactors that may optionally be used are heparin, hyaluronic acid, a fibronectin, an elastin, a laminin, a proteoglycan, collagen, or gelatin, among others. In certain embodiments, a divalent cation, calcium chloride, zinc sulfate, magnesium chloride, heparin, sodium bicarbonate, sodium chloride, or sodium phosphate may be added as a cofactor to treated cells. In some embodiments, a protein or a protein fragment may be a cofactor that is added to treated cells. In further embodiments, a protease described herein may be a cofactor that is added to treated cells.

In certain embodiments, treated cells that have been cryopreserved are optionally revived at a temperature between about 10° C. and about 37° C. before being applied to a tissue or an organ defect, a tissue, an organ, a matrix, or a mixture of two or more of these. In certain embodiments, treated cells may be combined with one or more body fluid, for example blood, platelet-rich plasma, plasma, bone marrow, and cord blood, among others, and an isotonic, hypotonic, or hypertonic solution, for instance saline, or Lactated ringer solution, and others, before they are used to treat a tissue or an organ defect. In some embodiments, treated cells may be applied to a tissue or an organ defect by injecting or inserting the cells between tissues or organs, or placing the cells on top of the defect. Modified growth factors may be administered to cells in vitro, in vivo, or in situ, in some embodiments. The modified growth factors may be administered to cells that are in tissue or organ or that have been isolated from tissues or organs, in some embodiments. In certain embodiments, at least one modified growth factor or compositions described herein may be administered to cells in (1) a cell culture medium, (2) a tissue or an organ, (3) a matrix, or (4) a combination of two or more of these.

There are a variety of osteoblast or chondrocyte differentiation markers that can be measured to assess osteoinductivity or chondroinductivity, respectively. For example, cells express alkaline phosphatases during the early stages of differentiation toward osteoblast lineages. Therefore, in vitro alkaline phosphatase assays may be used to evaluate osteoinductivity in cells contacted with the modified growth factor peptide(s) of the present invention. The ability of the modified growth factor peptide(s) of the present invention to stimulate or induce the alkaline phosphatase expression in an otherwise non-bone forming cells, such as myoblast (C2C12 cells), would indicate that the modified growth factor peptide(s) of the present invention has osteoinductive activity. In these assays, cells cultured without added growth factors of any kind and without added modified growth factor peptide(s) of the present invention are used as negative controls to show that the baseline alkaline phosphatase expression on non-bone forming cells. The baseline of the osteoblastic markers in the negative control need not be zero, meaning that the cells in the negative control group may have at least some level of phenotypic marker(s) associated with osteoblasts. Accordingly, an "osteoinductive" peptide of the present invention would simply cause an increase in the predetermined osteoblastic markers in experimental cells over control. Similarly, chondrocyte markers, including but not limited to type X collagen, type II collagen, Sox 9, Aggrecan. Matrilin-1 and CEP-68, to name a few, can be used to assess chondroinductive potential.

Moreover, osteoinductivity and/or chondroinductivity may be determined in tissue culture by investigating the ability of the modified growth factor peptide(s) of the present invention to differentiate or induce osteoblast phenotype or chondrocyte phenotype in cultured cells, such as primary cells, cell lines, or explants. For example, the cells may display increased production of a marker characteristic of osteoblasts and/or chondrocytes, such as alkaline phosphatase, etc. For example, the osteoinductive or chondroinductive potentials of the modified growth factors may be more than 0.2, 0.4, 0.6, 0.8, 1, 2, 3, 4, 5, 6, 7, 8, 9 or 10 times greater for the modified growth factors compared to the unmodified growth factors. In another example, the osteoinductive or chondroinductive potentials of the modified growth factors may be more than 10, 20, 30, 40, 50, 60, 70, 80, 90, 100, 500 or even 1000 times greater for the modified growth factors compared to the unmodified growth factors. Of course, this indicates that lower concentrations of modified growth factor, compared to unmodified growth factor are required to achieve the same effects.

Osteoinductivity or chondroinductivity, for assessing the bone or cartilage forming potential induced by the modified growth factor peptide(s) of the present invention in a location such as muscle, may also be evaluated using a suitable animal model. For example, intramuscular implantation into a rodent has been used as a model to assess osteoinductive activity of bioactive factors.

The invention also relates to methods of promoting proliferation or maintaining the differentiated state of osteoblasts and/or chondrocytes and/or any cell type disclosed herein comprising administering to the osteoblasts or chondrocytes the modified growth factor peptides or compositions described herein. The proliferative activity of the novel peptides may or may not be altered, including but not limited to, enhanced activity, relative to the normal, mature growth factor.

Mitogenicity may be assessed by investigating cell proliferation induced by the modified growth factor peptides using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the modified growth factors. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as using a trypan blue hemacytometer.

The invention also relates to methods of increasing a cellular growth factor activity comprising administering to the cell at least one protease and the growth factor. The protease is a protease described herein, including, but not limited to, collagenase, clostripain, dispase, trypsin, BMP-1, MMP-13, and a mixture thereof. In some embodiments, the growth factor comprises the modified growth factor described herein. The cell is a cell described herein, including, but not limited to, differentiated cells, adult stem cells, progenitor cells, and induced pluripotent stem cells. As described previously, the modification of the growth factors as disclosed herein also enhances the activity of BMP-4. In certain embodiments, administering the protease along with the modified growth factor described herein further enhances the activity of the modified growth factor, such as an osteoinductive or chondroinductive activity.

In some embodiments, the addition of the protease described herein into the composition enhances stability of the growth factor in the same composition. As described previously, the modification of the growth factors as disclosed herein also enhances the stability of the growth factor. In certain embodiments, the addition of the protease into the composition comprising the modified growth factor further enhances the stability of the modified growth factor.

In additional embodiments, the composition administered to a cell in increasing a cellular growth factor activity comprises two or more protease. In some embodiments, a second protease can be mixed into the composition comprising the protease and the growth factor or can be administered separately from the composition comprising the protease and the growth factor.

The invention further relates to tissue or organ repair or regeneration compositions comprising at least one modified growth factor peptide and a tissue, an organ, a matrix and/or a mixture of two or more thereof. The tissue or organ repair composition may comprise demineralized bone and homogenized connective tissue.

An implantable biocompatible matrix for use with the compositions described herein can function as a suitable delivery or support system for the modified growth factor peptides. A biocompatible matrix should be non-toxic, non-eliciting or stimulating severe inflammatory response or immunological rejections, and devoid of other undesired reactions at the implantation site. Suitable matrices may also provide for release of the modified growth factor peptides, for example, to promote a slow, sustained release over time at the implantation site. In one embodiment, the matrix is a bone matrix or cartilage. In addition to its common, ordinary meaning, "administering to the matrix" includes embedding into the matrix or matrices host cells capable of producing at least one modified growth factors peptide. In another embodiment, the invention provides for methods of treating cells with at least one modified growth factor peptide or compositions described herein and implanting these treated cells into a matrix, such as, but not limited to a bone matrix or cartilage.

Suitable matrices include, but are not limited to, porous scaffolds into which bone cells or progenitor cells may migrate. Osteogenic or chondrogenic cells, i.e., cells involved in the process of deposition of new bone material or cartilagenous material, respectively, can often attach to such porous matrices, which can then serve as scaffolding for bone and cartilage tissue growth. For certain applications, the matrix should have sufficient mechanical strength to maintain its three dimensional structure and help support the immobilization of the bone segments being united or grafted together. Porous matrices which provide scaffolding for tissue growth can accelerate the deposition of new bone or the rate of bone growth and are said to be "osteoconductive." Osteoconductive matrices are especially useful in the pharmaceutical compositions described herein. Porous matrices which provide scaffolding for tissue growth can accelerate the deposition of new cartilage or the rate of cartilage growth and are said to be "chondroconductive." Osteoconductive matrices are especially useful in the pharmaceutical compositions described herein. Chondroconductive matrices are especially useful in the pharmaceutical compositions described herein. The osteoinductive or chondroinductive activity of the novel peptides may or may not be altered, including but not limited to, enhanced activity, relative to the normal, mature growth factor. Thus, the osteoconductive or chondroconductive activity of the treated matrices of the present invention may be enhanced compared to matrices not treated with modified growth factor. Of course, the matrices are considered to be osteoconductive or chondroconductive if cells within the matrix begin to differentiate into more osteoblast-like or chondrocyte-like appearing or functional cells, respectively.

Matrices can be derived from natural sources or they can be synthetic or a mixture of both. Matrices from natural sources may also comprise natural polymers, including, but not limited to, collagen, hyaluronic acid, alginate, albumin, fibrinogen-fibrin, chitosan, elasin, laminin, connective tissues, cortical or cancellous bone, demineralized or mineralized bone, fascia lata, dermis, muscle, ligament, tendon, a mixture thereof, and mixture of reconstituted tissue. Matrices from synthetic sources refer to any material not produced by living organisms, which may include, not limited to, the synthetic material made up of organic components, inorganic components, or a mixture thereof. In some embodiments, a synthetic matrix may comprise an organic synthetic polymer, such as poly(lactic-co-glycolic acid), polycaprolactone (PCL), polyglycolic acid (PGA), polylactic acid (PLA), polyhydroxybutyrate (PHB), Poly(ethylene glycol) (PEG), poly(ethylene oxide) (PEO)), and others. In some embodiments, a tissue, an organ, or matrix comprising at least one of alginate, chitosan, collagen, gelatin, hyaluronic acid, a fibronectin, an elastin, a laminin, and a proteoglycan may be employed. In certain embodiments, a matrix comprising inorganic components, such as hydroxyapatite, calcium sulfate, octacalcium phosphate, calcium phosphate, macroporous calcium metaphosphate ceramic, β-tricalcium phosphate, metal, metal alloy, and others, may be used. A matrix used in certain embodiments of the present invention may be prepared by demineralizing, decellularizing or devitalizing a tissue or an organ and cells may be seeded onto the matrix.

In some embodiments, at least one modified growth factor or compositions described herein may be applied to the matrix and may be incubated at conditions permitting the generation of a treated matrix. In some embodiments, incubation may be carried out at about 40° C. or lower, or between about 10° C. and about 37° C., or about 20° C. and about 37° C. Incubation may be carried out for between at least about 2 minutes and about 120 minutes, about 3 minutes and about 100 minutes, about 4 minutes and about 80 minutes, about 5 minutes and about 60 minutes, and about 5 minutes and about 30 minutes in certain embodiments. Incubation may be performed under static or dynamic conditions, such as with agitation, shaking, stirring, mixing, horizontal motion, rocking, and others.

In some embodiments of the present invention, a matrix may be lyophilized before at least one modified growth factor or compositions described herein are administered to it. In certain embodiments, one or more modified growth factors may be administered to a matrix, and the treated matrix may be subsequently lyophilized. The lyophilized, treated matrix can then be rehydrated before it is used. Further, the cells can be seeded onto the matrix before implantation.

Examples of suitable osteoconductive or chondroconductive matrices include but are not limited to, collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable matrices are commercially available, such as Collograft™ (Collagen Corporation), which is a mixture of hydroxyapatite, tricalcium phosphate and fibrillar collagen, and Interpore™ (Interpore International), which is a hydroxyapatite biomatrix formed by the conversion of marine coral calcium carbonate to crystalline hydroxyapatite.

A number of synthetic biodegradable polymers can serve as osteoconductive or chondroconductive matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society. Examples of these polymers include polyα-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In one embodiment, the matrices used in the compositions and methods of the present invention are bone matrices. As used herein, a bone matrix is a matrix derived from or including elements of natural bone. In some embodiments, the natural bone is mineralized, partially demineralized, demineralized, cancellous, cortical, or cortical cancellous bone. The bone matrices used herein may or may not include additional synthetic components not typically found in bone tissue. Other embodiments include compositions and methods utilizing a matrix derived from cartilage, other soft tissues such as the dermis, connective tissue, fascia, small intestine submucosa, serous membrane, pericardium, tendon, ligament, muscle, adipose tissue, myelin, blood vessels, base membrane, amniotic membrane and others. A matrix prepared from hyaline cartilage, fibrocartilage or elastic cartilage, may be employed in some embodiments. A matrix may be prepared from hyaline cartilage found in the condyle, tibial plateau, femoral head, humeral head, costal cartilage, or fibrocartilage found in intervertebral discs, or elastic cartilage found in the epiglottis or ear. In certain embodiments, a matrix derived from natural sources that has been optionally cleaned, disinfected, chemically modified, decellularized, particulated, homogenized, lyophilized, gamma ray irradiated, and/or plasticized may be used. Any of the matrices used herein may or may not include additional synthetic components not typically found in such tissue.

In one specific embodiment, the bone matrices or cartilage matrices may be demineralized or decellularized, respectively. Examples of demineralized matrices and methods of making are described in U.S. Pat. Nos. 6,189,537 and 6,305,379.

The matrix, tissue, or organ used in certain embodiments of the present invention may be in the form of a powder, particulates, sheets, fibers, gels, putties, paste, blocks, cylinders, sponges, meshes, films, slices, curls, flakes, or wedges, among others. In certain embodiments of the present invention the matrix, tissue, or organ comprising the modified growth factor peptide(s) may be in the form of a powder, fibers, putty, or a sponge. In further embodiments, the sponge can include, for example, the implant having sponge-like structures disclosed in the co-pending, commonly-assigned patent application PCT/US09/04556 entitled "Composition for a Tissue Repair Implant and Methods of Making the Same" filed on Aug. 7, 2009. The treated matrices can be used in any of the methods of the present invention.

The invention also relates to methods of increasing or promoting osteogenesis or chondrogenesis in cells. The methods may comprise treating the cells in matrices with at least one of the modified growth factor peptides or compositions described herein. As used herein, "osteogenesis" is the deposition new bone material or formation of new bone, including, but not limited to, intramembranous osteogenesis and endochondral osteogenesis. As used herein, "chondrogenesis" is the deposition new cartilage material or formation of new cartilage. The osteogenic or chondrogenic inducing activity of the novel peptides may or may not be altered, including but not limited to, enhanced activity, relative to the normal, mature growth factor. The cells to which the modified growth factors may be administered include cells in any tissue in which bone or cartilage formation is desired, such as, but not limited to, bone, cartilage, ligament, muscle, etc.

The invention also relates to methods of treating a tissue or organ defect or injury, for example, a musculoskeletal, dental or soft-tissue defect or injury, in an animal comprising administering (1) cells cultured in the presence of one or more modified growth factors or compositions described herein and/or (2) one or more modified growth factors or compositions described herein to the tissue or organ defect.

The invention further relates to methods of treating a tissue or an organ defect or injury, for example a musculoskeletal, dental or soft-tissue defect, in an animal by applying a treated matrix to the defect, and application to the defect may be accomplished by injecting the treated matrix into the defect, inserting the treated matrix between tissue or organ, or placing the treated matrix on top of the defect. The present invention is also directed to treating a defect or injury in an organ in a similar manner. At least one cofactor may be added to a treated matrix, such as a matrix comprising a modified growth factor, in some embodiments.

In yet another embodiment, cells may be seeded onto a treated matrix. The cells seeded on the treated matrix can be any cell, such as but not limited to, osteoblasts, chondrocytes, progenitor cells, and stem cells disclosed herein or otherwise known in the art. The seeded cells may be allowed to proliferate and possibly attach to the matrix. Methods of seeding cells onto matrices, such as collagen, are well known in the art. Alternatively, cells may first be treated with at least one modified growth factor or compositions described herein and the treated cells may then be seeded onto a treated or untreated matrix.

Any of the methods of the present invention can be performed in virtually any setting, such as an in vivo, ex vivo, in situ or in vitro setting. For example, methods of promoting osteogenesis in cells may be performed in cell culture, or may be performed in an intact organism. Moreover, any combination of any two or more of any of the embodiments described herein are contemplated.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

The following examples are illustrative and are not intended to limit the scope of the invention described herein.

Example 1

Preparation and Sequencing of Modified BMP-4

Collagenase (Sigma Aldrich) was linked to sepharose beads and the un-bound collagenase was removed by extensive washing. Collagenase linked-sepharose beads were used to treat mature rhBMP-4 by incubation at 37° C. overnight with gentle mixing. The treated mature rhBMP-4 was separated by SDS-PAGE gel electrophoresis followed by protein transferring onto PVDF membrane. The proteins on PVDF membrane were stained by Coomassie blue and the related bands were cut for N-terminal sequencing using Edman degradation chemistry with an ABI Procise 494 sequencer. Proteins on PVDF membrane were also detected by Western Blot using antibody against C-terminus of rhBMP-4.

By comparing the collagenase treated mature rhBMP-4 bands with the untreated mature rhBMP-4 control bands, extra bands at around 17-22 kDa were cut for N-terminal sequencing. Ten amino acids of the N-terminus of the collagenase treated mature rhBMP-4 were detected using Edman degradation chemistry with an ABI Procise® 494 sequencer. The deduced amino acid sequence of the N-terminus of the treated rhBMP-4 was KKNKNCRRHS (SEQ ID NO: 7). The N-terminus of the treated rhBMP-4 matched the untreated mature rhBMP-4 sequence, indicating that the collagenase cleaved the mature BMP-4 after the first 10 amino acids. The Western blot detected a band for collagenase treated rhBMP-4 group, which is about 1-2 kDa smaller than the band for untreated mature rhBMP-4.

Example 2

Osteoinductive Potential of Modified rhBMP-4

Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C. C2C12 cells (ATCC CRL-1772) were seeded at a density of about 25,000 cells/cm$^2$ in 24-well plates on day one. Collagenase and various concentrations of mature rhBMP4 were mixed in microcentrifuge tubes at molarity ratios between about 1:10 and about 1000:1 and incubated at 37° C. overnight. The collagenase-treated rhBMP-4 or untreated rhBMP4 was introduced into each well of the C2C12 cell seeded 24-well plate on day two. The final concentrations of rhBMP4 were 1, 5, 10, and 30 ng/mL. After 3 days of incubation at 37° C. and 5% $CO_2$, cells were collected from culture plates and cell lysates were prepared for AP assays and BCA total protein assays.

The results of the in vitro AP assay are shown in FIG. 1. When cells were cultured with treated or untreated mature rhBMP-4 at a concentration of 10 ng/mL or less, the differences in alkaline phosphatase activity were negligible. At a concentration of 30 ng/mL, cells treated with collagenase-treated rhBMP-4 expressed significantly higher AP activities than those treated with untreated mature rhBMP-4.

Example 3

Osteoinductive Potential of Modified rhBMP-4 with or without a Protease

C2C12 cells (ATCC CRL-1772), which are from a mouse myoblast cell line, are seeded at a density of 25,000 cells/cm$^2$ in 24-well plates on day one. Collagenase and rhBMP-4 are mixed in microcentrifuge tubes at a molarity ratio of between about 1:10 and about 100:1 and are incubated overnight at 37° C. The treated mature rhBMP-4 is aliquoted with or without further HPLC purification described above. The aliquot with further HPLC purification (purified modified BMP-4) is quantified by ELISA. The aliquot without further HPLC purification (non-purified modified BMP-4) retained the collagenase in the aliquot. The aliquots are used to test the effect of treated mature rhBMP-4 on osteogenic potential of C2C12 myoblasts.

Each of the rhBMP-4 control, and the purified modified rhBMP-4, and the non-purified modified rhBMP-4 at the same concentration is introduced into wells of the C2C12 cell seeded 24-well plate. C2C12 cells cultured in media alone (without addition of rhBMP-4 or modified rhBMP-4) are used as a negative control.

After 3 days incubation at 37° C., 5% $CO_2$, the AP assay as described above is performed. The alkaline phosphatase activity of cells cultured with the purified modified rhBMP-4 or the non-purified modified rhBMP-4 are significantly higher than that of cells cultured with non-treated rhBMP-4 control. The alkaline phosphatase activity of cells cultured with non-purified modified rhBMP-4 is also significantly higher than that of cells cultured with purified modified rhBMP-4. The results demonstrate a significant increase in the alkaline phosphatase activity by administering the non-purified modified rhBMP-4 compared to administering the purified modified rhBMP-4.

Further, with another set of C2C12 cells cultured as described above, the purified modified rhBMP-4 is introduced into wells of the C2C12 cell along with 138 ng/mL of active dispase or inactive dispase, or 100 ug/mL collagenase or inactive collagenase. The AP assay as described above is performed, and the results show that adding active or inactive dispase or collagenase to the purified modified rhBMP-4 samples also increase the alkaline phosphatase activity.

In addition, rhBMP-4 treated by clostripain, dispase, and the mixture thereof, without further purification, also increase the alkaline phosphatase activity compared to non-modified rhBMP-4 control. In addition, rhBMP-4 treated by BMP1 or MMP13, without further purification, also increase the alkaline phosphatase activity compared to non-modified rhBMP-4 control.

Example 4

Osteoinductive Potential of Modified rhBMP-4 with a Protease

C2C12 cells (ATCC CRL-1772) are cultured as described above. Collagenase and rhBMP-4 are mixed in microcentrifuge tubes at a molarity ratio of between about 1:10 and about 100:1 and incubated overnight at 37° C. with agitation. The treated mature rhBMP-4 is aliquoted, and the aliquots are used to test the effect of treated mature rhBMP-4 on osteogenic potential of C2C12 myoblasts as follows.

For the osteoinductive potential assessment, base media of DMEM containing 1% FBS, 50 μg/mL of ascorbic acid and 10 mM of β-glycerolphosphate is used as a control group. The base media control with the addition of 50 ng/mL of rhBMP-4 is used as the BMP-4 positive control group. The base media control with the addition of 50 ng/mL of modified rhBMP-4 without the purification is used as the test group. The media are added into C2C12 cells seeded on chamber slides and changed every 3-4 days.

After several days of incubation at 37° C., 5% $CO_2$, photographs are also taken for cell cultures in each group. The nodule formation of C2C12 cells appear only in modified rhBMP-4 group, but not in the other two control groups. After more days of incubation, the media is removed from chamber slides and the slides are stained with Alizarin Red S. Alizarin red S is used to identify calcium-rich deposits by cells in culture or tissue sections, which indicates the effect of osteoinductive material on osteogenic potential of cells.

For the base media control group, no positive Alizarin red S staining is found at any tested time points. For the rhBMP-4 control group, some Alizarin red S staining is detected after 6 or 12 days of incubation. For the modified rhBMP-4 group, after 6 days of incubation, significant amount of nodules stain positive by Alizarin red S. After 12 days of incubation, more Alizarin red S positively stain nodules of larger size are observed in C2C12 cells cultured with modified rhBMP-4 than that in C2C12 cells cultured with unmodified rhBMP-4. This data suggests that modified rhBMP-4 has a significantly greater effect on osteogenic potential of C2C12 myoblasts as compared to the unmodified mature rhBMP-4 control.

Example 5

Stability of Modified rhBMP-4 with or without a Protease in Cell Culture

C2C12 cells are cultured, and purified and non-purified modified rhBMP-4 are prepared as described in Example 3 above. The purified modified rhBMP-4, the non-purified modified rhBMP-4, or the untreated mature rhBMP-4 at the same concentration is introduced into each well of the C2C12 cell seeded 24-well plate on day two. C2C12 cells cultured without addition of rhBMP-4 or modified rhBMP-4 are used as a negative control. After incubation at 37° C., 5% $CO_2$ for different durations (24 hr, 48 hr, or 72 hr), spent culture media are collected from these original 24-well plates and transferred into new 24-well plates containing fresh C2C12 cells seeded the previous day, and the new 24-well plates are incubated at 37° C., 5% $CO_2$ for another 3 days. Cells from the original 24-well plates and new 24-well plates are collected at the end of each culture period, and cell lysates are prepared for AP assays and BCA total protein assays.

For the control groups wherein C2C12 cells are cultured for three days in untreated rhBMP-4 spent media collected after 24 hrs, 48 hrs, and 72 hrs, the alkaline phosphatase activity is reduced as compared to that of cells cultured for three days with fresh rhBMP-4 media. For the experimental groups in which C2C12 cells are cultured for three days in purified modified rhBMP-4 spent media collected after 24 hrs, 48 hrs, and 72 hrs, the alkaline phosphatase activity is also reduced less than for the control group. For the experimental groups in which C2C12 cells are cultured for three days in non-purified modified rhBMP-4 spent media collected after 24 hrs, 48 hrs, and 72 hrs, however, the alkaline phosphatase activity is maintained at a similar or higher level as compared to that of cells cultured for three days with fresh non-purified modified rhBMP-4 media. This demonstrates that the presence of a protease can further enhance the stability of modified BMP-4 in culture media.

Example 6

Stability of Modified rhBMP-4 with or without a Protease on Shelf

Purified and non-purified modified rhBMP-4 is prepared as described in Example 3 above. Aliquots of the purified and non-purified modified rhBMP-4 at the same volume and concentration are incubated at 37° C. for different durations (2 days to 2 weeks). After each time point, one aliquot from each group is transferred into −20° C. freezer until the last time point is completed. The aliquots of purified modified rhBMP-4 or non-purified modified rhBMP-4 from different time points are introduced into each well of the C2C12 cell cultured as described above. C2C12 cells cultured without the addition of rhBMP-4 or collagenase are used as a negative control. After 3 days incubation at 37° C., 5% $CO_2$, the AP assay as described above is performed.

The alkaline phosphatase activity of cells cultured with purified modified rhBMP-4 on shelf (37° C.) for 7 days or 14 days is reduced as compared to that of cells cultured with purified modified rhBMP-4 on shelf (37° C.) for 2 days. The alkaline phosphatase activity of cells cultured with non-purified modified rhBMP-4 on shelf (37° C.) for 7 days or 14 days is reduced less than that of cells cultured with purified modified rhBMP-4. This demonstrates that the presence of a protease can further enhance the stability of modified BMP-4 on shelf.

What is claimed is:

1. A composition comprising a peptide consisting of the amino acid sequence of SEQ ID NO: 2, and at least one protease selected from the group consisting of collagenase, dispase, and a mixture thereof.

2. The composition according to claim 1, wherein the at least one protease consists of collagenase.

3. The composition of claim 1, wherein the at least one protease consists of dispase.

4. The composition of claim 1, wherein the at least one protease consists of collagenase and dispase.

5. The composition according to claim 1, wherein the concentration of the peptide is about 30 ng/mL or less.

6. The composition according to claim 1, wherein the concentration of the peptide is about 10 ng/mL or less.

7. The composition of claim 1, further comprising at least one pharmaceutically acceptable carrier.

8. The composition according to claim 7, wherein the pharmaceutically acceptable carrier is selected from the group consisting of saline, Ringer's solution, dextrose solution, 5% human serum albumin, dispersion media, coatings, antibacterial and antifungal agents, and isotonic and absorption delaying agents.

9. A method of promoting differentiation of cells into osteoblasts or chondrocytes, the method comprising treating the cells with the composition of claim 1 in an amount effective to promote the differentiation, wherein the cells are progenitor cells, adult stem cells, or induced pluripotent stem cells.

10. The method of claim 9, wherein the cells are progenitor cells or adult stem cells.

11. The method of claim 10, wherein the progenitor cells or the adult stem cells are derived from placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, or muscle.

12. The method of claim 9, wherein the cells are induced pluripotent stem cells.

13. A method of promoting osteogenesis in a tissue, the method comprising treating the tissue with the composition of claim 1 in an amount effective to promote the osteogenesis in the tissue, wherein the tissue is a bone tissue.

14. The method of claim 13, wherein the osteogenic activity of cells in the treated tissue is greater than the osteogenic activity of cells in untreated tissue.

15. A method of increasing a cellular growth factor activity in cells, the method comprising treating the cells with the composition of claim 1 in an amount effective to increase the cellular growth factor activity in the cells, wherein the cells are progenitor cells, adult stem cells, or induced pluripotent stem cells, and wherein the cellular growth factor activity is osteoinductive activity, chondroinductive activity, or a combination thereof.

16. The method according to claim 15, wherein the cells are progenitor cells or adult stem cells.

17. The method according to claim 16, wherein the progenitor cells or the adult stem cells are derived from placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, or muscle.

18. The method according to claim 15, wherein the cells are induced pluripotent stem cells.

19. The method according to claim 15, wherein the composition comprises two or more proteases.

20. The method according to claim 19, wherein the composition comprises (a) a first protease selected from the group consisting of collagenase, clostripain, dispase, trypsin, MMP-13 (matrix metalloproteinase-13), and a mixture thereof, and (b) a second protease selected from the group consisting of collagenase, clostripain, dispase, trypsin, BMP-1 (bone morphogenetic protein-1), MMP-13 (matrix metalloproteinase-13), and a mixture thereof, and wherein the first and second proteases are different.

21. The method according to claim 15, wherein the at least one protease is collagenase.

22. A method of growing and/or culturing cells comprising:
growing and/or culturing cells in the presence of the composition of claim 1.

23. The method according to claim 22, wherein the cells are selected from the group consisting of mesenchymal stem cells, adipose-derived stem cells, embryonic stem cells, progenitor cells, differentiated cells, undifferentiated cells, and induced pluripotent stem cells.

24. A method of making the composition of claim 1, comprising preparing said peptide by contacting mature BMP-4 with collagenase under conditions that promote protein cleavage to produce the peptide and harvesting the peptide, and
mixing the peptide with at least one pharmaceutically acceptable carrier and the at least one protease, whereby the composition of claim 1 is prepared.

25. A method of making the composition of claim 1, comprising
preparing said peptide by culturing a host cell under conditions suitable for protein expression, wherein the host cell comprises a vector that encodes said peptide,
harvesting the peptide, and
mixing the peptide with the at least one protease, whereby the composition of claim 1 is prepared.

* * * * *